United States Patent
Yeh et al.

(10) Patent No.: US 8,087,780 B2
(45) Date of Patent: Jan. 3, 2012

(54) HIGH PRECISION VISUAL FIELD TESTER WITH UNPRECEDENTED DETAILED RESULTS

(76) Inventors: Hsu-Chieh Yeh, Monroeville, PA (US); Ming-Yuan Yeh, San Jose, CA (US)

( * ) Notice: Subject to any disclaimer, the term of this patent is extended or adjusted under 35 U.S.C. 154(b) by 534 days.

(21) Appl. No.: 11/496,167

(22) Filed: Jul. 31, 2006

(65) Prior Publication Data

US 2008/0024726 A1 Jan. 31, 2008

(51) Int. Cl.
*A61B 3/02* (2006.01)
*A61B 3/10* (2006.01)
(52) U.S. Cl. .................................. 351/218; 351/224
(58) Field of Classification Search ........... 351/221–224
See application file for complete search history.

(56) References Cited

U.S. PATENT DOCUMENTS

| | | | |
|---|---|---|---|
| 3,946,664 A * | 3/1976 | Peckinpaugh et al. | 101/41 |
| 3,951,062 A * | 4/1976 | Abramson | 101/483 |
| 4,787,247 A * | 11/1988 | Wuchinich et al. | 73/620 |
| 6,572,229 B2 * | 6/2003 | Wei | 351/211 |
| 6,736,511 B2 * | 5/2004 | Plummer et al. | 351/224 |
| 7,329,003 B2 * | 2/2008 | Nicolini | 351/244 |
| 2007/0182928 A1 * | 8/2007 | Sabel | 351/224 |

* cited by examiner

*Primary Examiner* — Scott J Sugarman
*Assistant Examiner* — Brandi Thomas

(57) ABSTRACT

A visual field testing apparatus for scanning the visual field of a human eye in great detail, precision, and clarity so as to detect the smallest blind area whereby allowing users the ability of early detection of glaucoma and other eye diseases of visual loss. The apparatus is small and inexpensive so that anyone can afford to purchase it and self-test without assistance so that the user can test frequently at home which further leads to early detection of eye diseases. Because of its great precision and detail in test results, the present invention is especially useful to doctors and researchers. One embodiment of the present invention is a visual field tester which comprises: (a) a recording surface having eye fixation means to fixate an eye's visual field relative to said recording surface; (b) a handheld scanning device which has a test mark for detecting very small blind areas in said eye's visual field and marking means for mapping said detected very small blind areas onto said recording surface; and (c) a head support for supporting a user's head.

7 Claims, 8 Drawing Sheets

HIGH PRECISION VISUAL FIELD TESTER WITH UNPRECEDENTED DETAILED RESULTS

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

This invention relates to a device and a method for detecting and mapping the diseased blind areas in a person's vision. The most widely used visual field tester today is the Standard Automated Perimeter (SAP) which is used to perform a contrast sensitivity test. In this test, a person is usually seated in front of a hemispherical projection surface whereupon an optical projection system projects circular spots according to an algorithm, and the subject responds to the stimulus by pressing an input device such as a mouse. Usually the algorithm used to project the spots of light is written so that the location and the timing of the projected lights are random to the user. This is to keep the user from falling into a rhythm and expectantly clicking on the input device even when he or she does not see the projected light. However, these SAP tests suffer from a number of disadvantages.

a) They are costly and most individuals would normally not be able to afford them. SAP equipment require an expensive projection system, software and hardware. The SAPs are usually only found at hospitals and eye physicians' offices. As a result, SAPs are not easily accessible devices. If someone wanted to monitor the condition of one's own visual field, he or she would not be able to run a visual field test often and usually would have to make an appointment with a doctor to do so.

b) SAPs are large bulky machines. They are not mobile machines that can be transported anywhere. Current SAPs are large and heavy and once they are placed at a certain location they cannot be moved easily.

c) SAPs are prone to inaccuracies and sometimes do not detect problems in the visual field until noticeable deterioration has occurred. One of the problems with SAPs is that due to the random generation of projected lights, users do not know where the next light will appear; therefore, sometimes they will often miss identifying certain lights because they were not prepared. The SAP tests are time-constrained; while a user is pondering whether or not to click the button, the next light appears. Therefore, it is a man-machine contest with the user being quite nervous in taking the test. Also, some machines require the user to fixate his or her eye on a bright light in order to keep the eye from wandering. However, blinking often creates after-images which tricks subjects into seeing a projected light where none was projected.

d) The result from SAPs do not show decisive results for each location in the visual field. Due to the inaccuracies in the SAPs, their algorithm usually displays or prints out a map of the visual field with each area of the visual field given different probabilities of damage or problems. This is done to account for the user's errors in clicking or identifying random lights. If the user did not click the button when a light was projected, the result from the SAP would be inaccurate. Rather than identifying an area where the subject could not see as a problem area, the SAP might identify it as an area with medium probability, but not definite probability.

e) Current visual field testers are not good at early detection of glaucoma or other eye diseases. If glaucoma can be detected early on, medication such as pressure-reducing eye drops can be given to stop the farther destruction of optical nerves in the eye. Often, when glaucoma is detected, excessive damage to the nerves in the eye has already occurred causing severe visual field loss. Because of the uncertain outputs from SAP testers, doctors and patients are often misled into believing glaucoma does not exist, when in actuality, it is already present. For example, a doctor may look at a result from a SAP and incorrectly conclude that an area with medium probability next to the natural blind spot is not problematic and is considered part of the natural blind spot when in reality, nerve cells have already begun to die in that region as is shown in the later section under the title "Accurate Detection of Diseased Blind Areas: FIGS. 6A-6B."

OBJECTS

Accordingly, to overcome the disadvantages of current visual field testers as described above, and besides the objects of the visual field device described in our patent, several objects and advantages of the present patent are:

a) To provide a visual field tester which can detect glaucoma and other eye diseases causing vision loss in their very early stages by scanning the visual field in even greater detail and accuracy, thus allowing early treatment.

b) To provide a visual field tester which can provide a decisive output, indicating which areas in the visual field are definitely good and which areas are definitely bad.

c) To provide an accurate visual field tester that allows the user to have total control so that he or she can retest certain areas of the visual field if he or she finds something unusual or feels that an area has been missed.

d) To provide an inexpensive visual field tester that anyone can afford and purchase readily.

e) To provide a small portable visual field tester that can be easily transported.

f) To provide precise and detailed visual field test results for a patient whereby his or her doctor can make a correct diagnosis.

g) To provide accurate and detailed visual field mapping results to help researchers track the progression of eye diseases under different treatments and to help them find new cures and root causes of eye diseases.

BRIEF SUMMARY OF THE INVENTION

The object of the present invention is to provide a new visual field tester for detecting, with decisive accuracy, glaucoma and other eye diseases with vision loss at the very early stages, and to provide a portable, inexpensive visual field tester that anyone can afford.

The invention includes a recording surface (typically a visual field grid sheet), a handheld scanning device, and an optional head support for reproducible test results.

The head support is comprised of a flat rigid frame with a T-shaped opening for a face and four support members. Under normal operation, the user would be seated or standing at a table with the visual field tester placed near the edge of the table. A user inserts his or her face into the T-shaped opening of the head support and positions the head using a mirror to align the center of the face with a line on the bottom-side of the head support. In this way, the head support allows the head to be positioned exactly the same distance and orientation from a recording surface or visual field grid sheet each time, so that the test is repeatable and the progression of the eye disease can be evaluated by comparing results of each test.

The visual field grid sheet itself is in polar coordinates comprised of an eye fixation mark at the center, radial lines, and concentric circles centered about the eye fixation mark. The concentric circles are corresponding to the visual angles of the eye under test. We shall refer to the blind area in a person's eye that corresponds to the area where the optic nerve joins the eye as the "natural blind spot" to follow conventional naming, and we shall refer to very small test areas that cannot be seen by the eye within the natural blind spot as "very small natural blind areas." We shall refer to very small test areas that cannot be seen by the eye outside of the natural blind area as "very small diseased blind areas." Likewise, we shall refer to a cluster of very small diseased blind areas as a "diseased blind area." Also, we shall use the term "very small blind area" to refer to a very small blind area which could either be a very small diseased blind area or a very small natural blind area. During scanning, the user would focus one eye on the eye fixation mark of the visual field grid sheet while the other eye is closed, and he or she would use a handheld scanning device to scan through all areas of the visual field and find areas of very small diseased blind areas and very small natural blind areas. The handheld scanning device has a block for a hand to hold. Protruding from the block is a thin resilient stick with a small test mark, usually a small dot, on the top surface at the end of the stick. Directly below the test mark is a stamp the same size and shape as the test mark. During scanning whenever the test mark disappears from view, the user would push down on the stick with the index finger and stamp a corresponding mark or dot onto the visual field grid sheet. The user could follow one of several methodological ways of scanning the visual field grid sheet without missing any areas. The visual field grid sheet is divided by circles of visual angles and radial lines of polar angles into many small sections which facilitates the user to search thoroughly for diseased blind spots in a particular section. Unlike tests done with SAPs which are controlled by the machine, in the present invention, users can spend as much time as they need to scan a particular spot so that they are sure the spot is a very small diseased blind area before stamping a dot or mark on the visual field grid sheet. At the end of the test, the user will have an extremely detailed map of the visual field. When the test mark is in a completely blind area, including both the diseased blind area and the natural blind spot, the user cannot see the test mark at all. As soon as the test mark is moved away from a completely blind area, the user can see the test mark clearly. Thus the user can map the contours of both the diseased blind area(s) and the natural blind spot clearly and precisely, and be able to distinguish the two areas easily as will be shown later. Furthermore, the test mark can be made as small as the user can see; thus, very small diseased blind areas, typically in the early stage of the disease, can be detected. Therefore, the present invention enables early detection of glaucoma and other eye diseases with vision loss and the ability to monitor progression of eye diseases.

ADVANTAGES

In some cases a diseased blind area may not be completely blind, that is, the area has both dead and intact optical nerves intermingled together. In this case, to the user's eye, the test mark would appear to be grey if the test mark is black, or the test mark would twinkle as it is moved around slowly, and the user would use a different color to stamp a mark to map the very small blind area on the visual field grid sheet. Thus, our visual field tester can map both the areas of complete blindness and the areas of partial blindness. This is especially important when later the user finds that a partially blind area becomes completely blind indicating his/her disease is getting worse, although the overall blind area does not grow larger.

From the description above, a number of advantages of our visual field tester become evident.

a) With our visual tester, the user can detect and locate a very small diseased blind area. That is, glaucoma and other eye diseases with vision loss can be detected at a very early stage, enabling the disease to be treated at a very early stage and preventing the eye from further vision loss beyond this early stage.

b) Furthermore, the visual field tester can be cheaply made so that everyone can afford to possess it and use it as frequently as he or she wants, which increases the chance for early detection of the disease.

c) The user can re-scan certain regions of his or her visual field and use smaller test marks or dots to obtain a visual field map with even finer resolution. In certain spots in the visual field that seem to be trouble spots, the user can retest those areas several times to ensure accurate results.

d) The output from our visual field tester shows exactly which areas of the visual field have problems and does not arrive at results based on a probability.

e) With our visual field tester the user can map not only completely blind areas, but also partially blind areas. Therefore, if a user's partially blind area becomes completely blind even though the overall blind area does not get larger, he or she will know the eye disease is getting worse.

CONCLUSION, RAMIFICATIONS AND SCOPE

Accordingly, a visual field test can be performed by anyone anywhere using the visual field tester described in this patent. In addition, the visual field tester of the present invention has the additional features in that:

it allows production of visual field testers at low cost, allowing individuals, rather than only hospitals and doctors to purchase them.

it permits a visual field tester to be compact and portable.

it provides a visual field tester that will give extremely accurate results as patients can rerun the test themselves on trouble spots by using a smaller test mark for finer resolution.

it gives decisive results on whether a specific area in the visual field has problems.

Although the description above contains many specifications, these should not be construed as limiting the scope of the invention but as merely providing illustrations of some of the presently preferred embodiments of the invention. Thus, the scope of the invention should be determined by the appended claims and their legal equivalents rather than by the examples given.

BRIEF DESCRIPTIONS OF THE DRAWINGS

DETAILED DESCRIPTION OF THE INVENTION

Description: FIGS. 1-4

Figure 1:
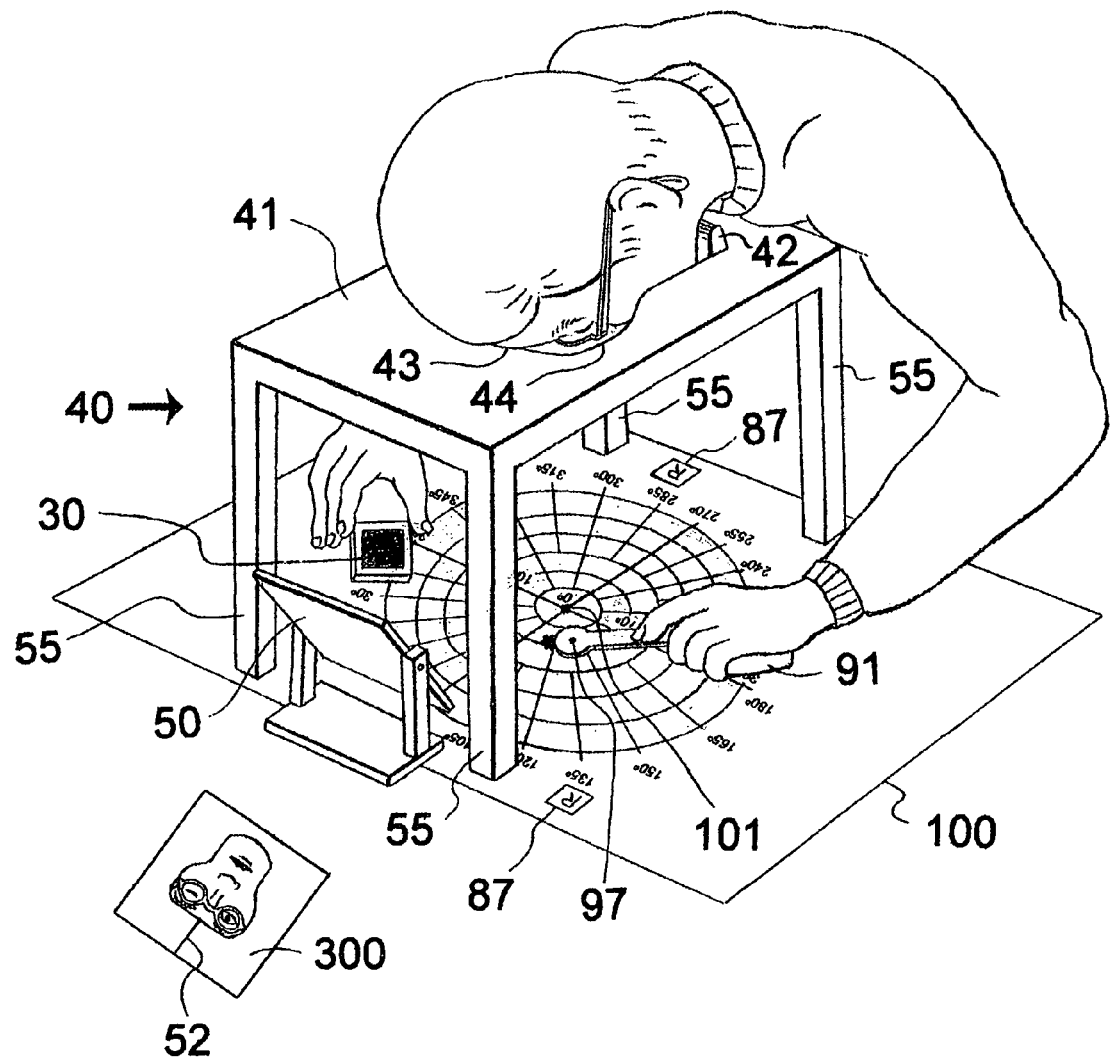
FIG. 1 illustrates the major components of the visual field tester according to the present invention and how it is used by a user.
Figure 2:
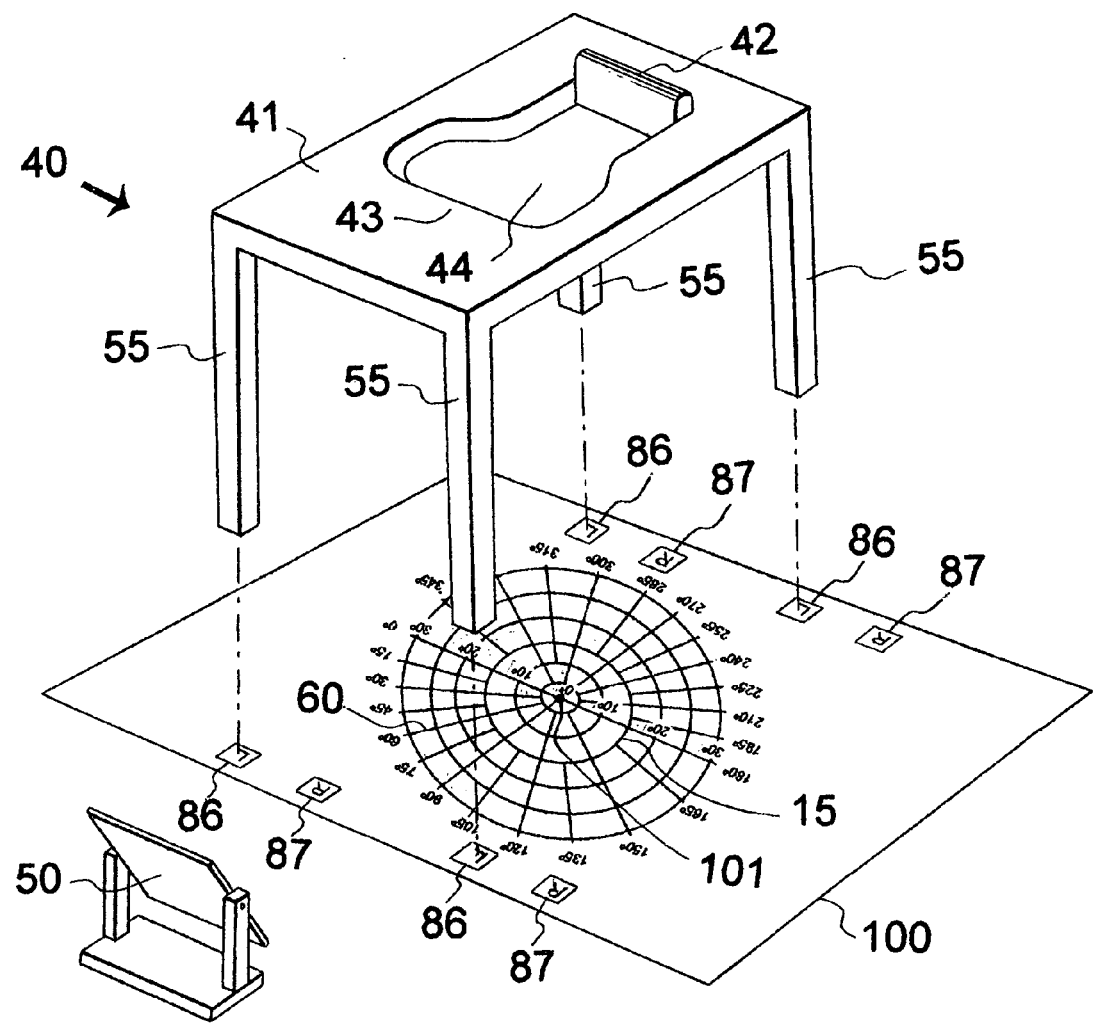
FIG. 2 is an exploded view of the visual field tester shown in FIG. 1, without the handheld scanning device which is shown in FIGS. 4A, B and C.
Figure 3:
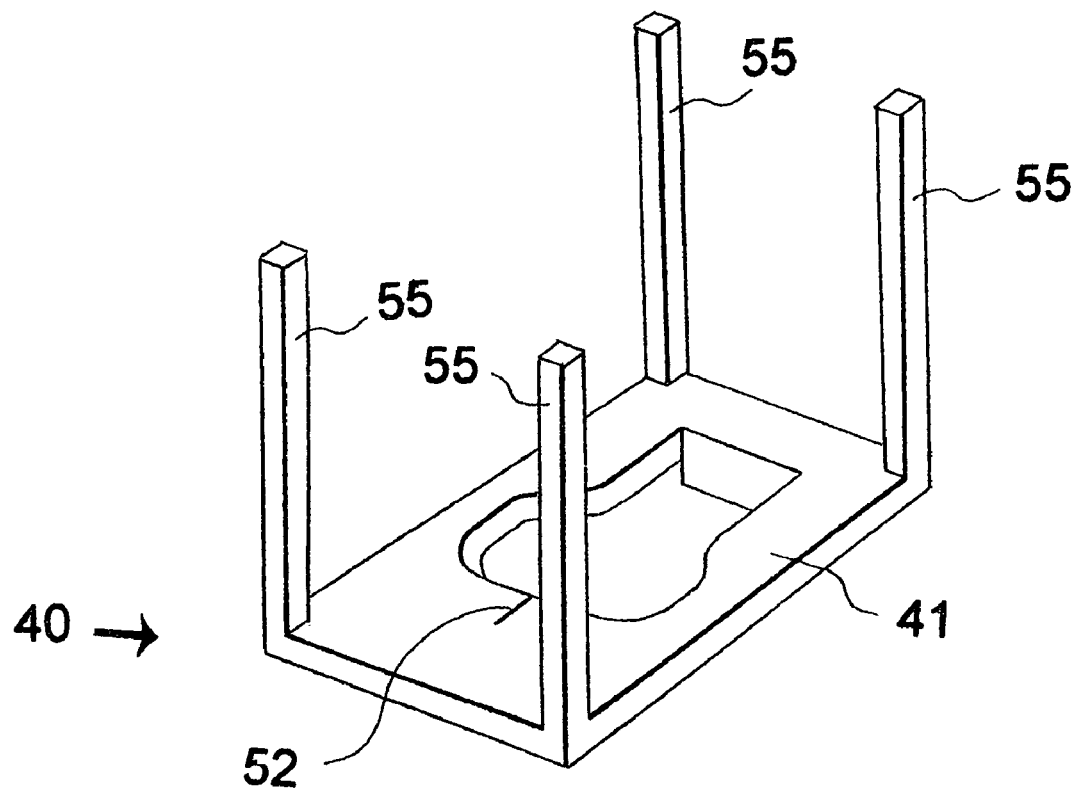
FIG. 3 shows that an alignment line is on the bottom of the rigid frame.

A preferred embodiment of the present invention is illustrated in FIG. 1 and FIG. 2. A user positions his or her head using a head support 40. The preferred embodiment's head support 40 can position the head the same orientation and location relative to a recording surface (typically visual field grid sheet 100) each time the test is performed. Thus, each time the user takes a visual field test with the present invention, the visual field tester's mapping results would be reproducible, and any changes in the visual field would show up as a change in the test results as compared to the previous one. If the user chooses, he or she could run the test without using the head support. He or she would place visual field grid sheet 100 (recording surface) on a flat surface such as a table, keep the head a fixed distance from sheet 100, and hold the head still while performing the test. The disadvantage of not using the head support is that if the user later wishes to perform additional tests, results would not be reproducible in that the map of the blind spots would not have the same reference point. Head support 40 consists of a rigid frame 41, and a tilting mirror 50.

A user inserts his or her face into face opening 44 that is located on rigid frame 41. At one end of face opening 44, a chin positioner 42 protrudes vertically from rigid frame 41. On the opposite side of face opening 44 is alignment line 52 (FIG. 3) on the bottom of rigid frame 41 that the user aligns with the center line of the user's face as he or she looks at mirror 50 as shown on the image 300 of mirror 50 on FIG. 1. Face opening 44 is T-shaped. Rigid frame 41 supports the user's head at three points: the forehead and two cheeks. The user's two cheeks rest on two sides of the narrow part of T-shape face opening 44 and the user's forehead rests on the front edge 43 of the wide part of T-shape face opening 44 as shown in FIG. 1. The wide part of T-shape opening 44 is wide enough to accommodate the user's eyes with glasses on.

Figure 4A:
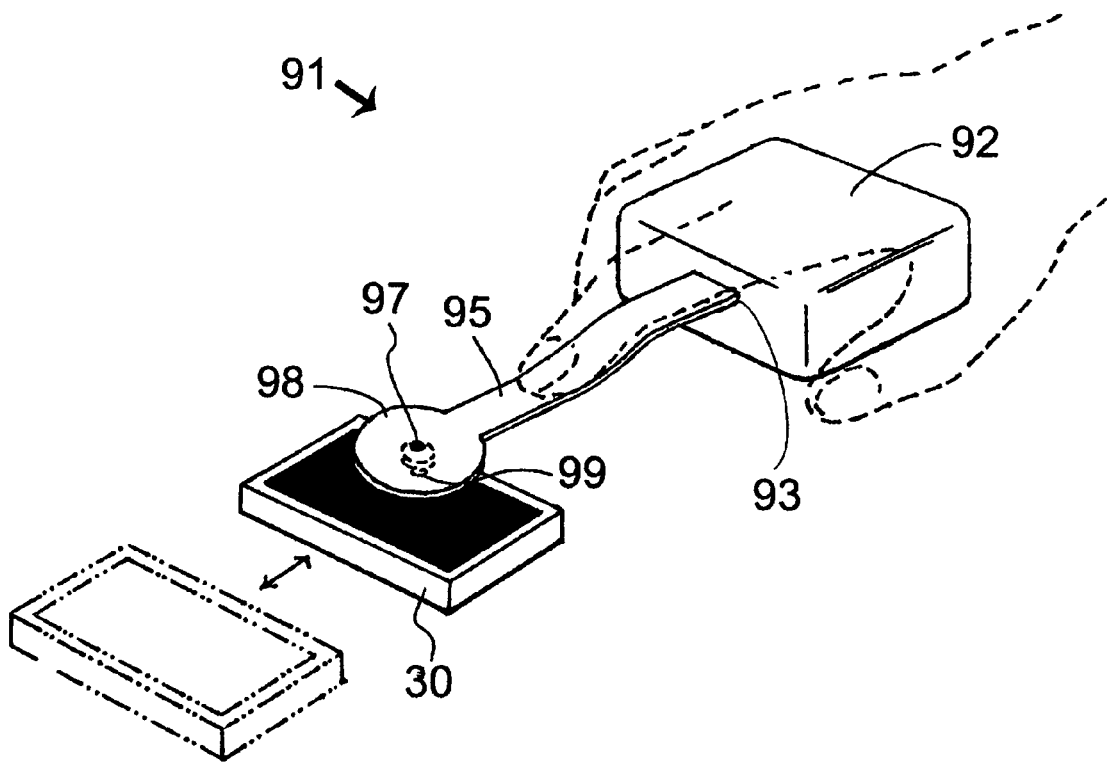
FIG. 4A is a perspective view of the handheld scanning device of the visual field tester.
Figure 4B:
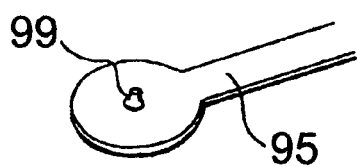
FIG. 4B is a view of the underside of the resilient stick of the visual field tester where a stamp is located.
Figure 4C:
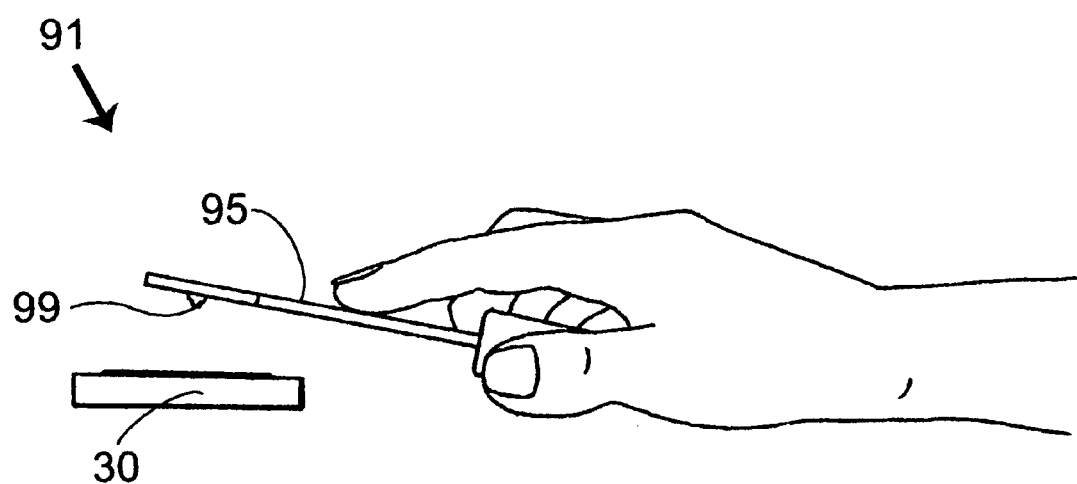
FIG. 4C is a side view of a user rewetting ink to the stamp on the handheld scanning device.

FIGS. 4A-4C show a preferred embodiment of a handheld scanning device 91. It consists of a hand holder 92, a resilient stick 95 inserted into an insertion hole 93 of hand holder 92, and an inkpad 30. On one end of resilient stick 95 is an enlarged area 98, typically the shape of a circular disc. A test mark 97 is on the top side of enlarged area 98. A stamp 99 is affixed directly beneath test mark 97 on the bottom side of enlarged area 98. Resilient stick 95 can be changed to another stick with test mark 97 of different size and corresponding stamp 99 of corresponding size if the user wishes to. For example, if the blind area in the user's visual field is quite large, he or she may use a resilient stick with a larger test mark or dot for faster scanning and then change to a stick with a smaller mark or dot for detailed scanning on the contour of the blind area.

FIG. 2 shows visual field grid sheet 100 (recording surface). An eye fixation mark 101 is located at the center of sheet 100. Centered about fixation point 101 are several concentric circles corresponding to the visual angles of the eye under test. The visual angle can be calculated from the formula:

$$\text{Visual angle} = \tan^{-1}(r/h)$$

where r is the radius of a circle of a given visual angle and h is the vertical distance between the tested eye and the fixation point 101 where the tested eye is approximately vertically above the fixation point 101. For example, a circle 15 corresponds to visual angle 15 degrees. Lines radiating from the eye fixation mark correspond to the polar angles of the test eye. For example, a radial line 60 corresponds to polar angle 60 degrees.

To test the left eye, four support members 55 of head support 40 are placed on areas 86 on grid sheet 100 so that the left eye is directly above fixation point 101. Likewise, to test the right eye, four support members 55 are placed on areas 87.

Operation: FIGS. 1-4

To use the present invention, the user first puts visual field grid sheet 100 (recording surface) on a table. Then he or she places head support 40 on visual field grid 100 with four support members 55 on areas 86 for testing the left eye and on areas 87 for testing the right eye. The user would then look at tilting mirror 50 and position the head until the center line (symmetric line) of his or her face aligns to alignment line 52 underneath rigid frame 41 (shown in mirror image 300 in FIG. 1). Once the head is positioned, the user stares with the test eye (the other eye is closed) at fixation point 101 located at the center of visual field grid sheet 100 (recording surface). FIG. 1 illustrates the testing of the left eye. This invention is for the person with central part of the visual field intact so that he or she can see fixation point 101. This is the case for normal persons and glaucoma patients and some other eye deceased patients.

Using the right hand or left hand, the user would grasp handheld scanning device 91, and slide it systematically on visual field grid sheet 100 such that the movement of test mark 97 would encompass the whole visual field. As the user moves handheld scanning device 91, he or she would keep the test eye staring at fixation point 101 while using the test eye's peripheral vision to see test mark 97. If test mark 97 disappears from the test eye's peripheral vision, it means that there is a blind spot that he or she cannot see test mark 97. The user should then stop moving handheld scanning device 91 immediately and presses down resilient stick 95 which will in turn cause stamp 99 to stamp a mark or dot on visual field grid sheet 100 (recording surface). The user can either use a finger of the hand that is holding handheld scanning device 91 or any finger of the other hand to press resilient stick 95. The user not being able to see test mark 97 with the peripheral vision indicates that the user has a very small blind area in the visual field, and by stamping the corresponding mark on visual field grid sheet 100, the user maps the very small blind area onto visual field grid sheet 100.

After test mark 97's movement covers the entire visual field grid sheet 100 and all very small blind areas found have been stamped, the complete map of very small blind areas in the visual field of the eye just tested is obtained. In the course of scanning, instead of test mark 97 completely disappearing, the user may find that test mark 97 does not disappear completely at a particular spot. This is because the very small blind area is smaller than test mark 97. For better resolution, the user would change resilient stick 95 (shown in FIG. 4A) to one with a smaller test mark 97. For this purpose, the present invention includes several resilient sticks 95 with different sizes of test marks 97, and resilient stick 95 can be easily changed by pulling out existing resilient stick 95 from insertion hole 93 in hand holder 92 in FIG. 4A and pushing in another resilient stick 95 into insertion hole 93. Thus the present invention can detect a very small blind area in the earliest stage of eye disease with vision loss.

If the user finds that test mark 97 twinkles as it is moved around slowly, then the area being scanned is an incompletely or partially blind area. That is, there are many dead optical nerves and intact optical nerves intermingled. In this case, the user would use a different color to stamp the very small blind area on the visual field grid sheet. Later, if the user cannot even see test mark 97 twinkling in that area, then the user and the eye doctor would know that the area became completely blind, and that the eye disease is getting worse even though the overall blind area did not enlarge.

To rewet stamp 99 with ink, the user tilts hand holder 92 up slightly so that stamp 99 is tilted up to allow inkpad 30 to slide beneath stamp 99 as shown in FIG. 4C. The user presses down resilient stick 95, and stamp 99 touches inkpad 30 to rewet stamp 99 with ink. Resilient stick 95 is made of resilient material, typically metal or plastic so that it will rebound and return to the original shape after being pressed down and released. Once stamp 99 is rewetted, it can stamp several times before it needs to rewet again. Therefore, it can stamp very fast in a blind region.

Stick 95 and enlarged area 98 (excluding test mark 97) have the same color as visual field grid sheet 100, typically white, to allow them to camouflage with the visual field grid sheet 100 during scanning. The reason for having enlarged area 98 is that during scanning, the user will only perceive the movement of test mark 97, and all surrounding stamped marks and grid lines will be blocked out by enlarged area 98.

The ink used for inkpad 30 can be any color. One way of tracking the progression of an eye disease is to use different colored ink every time the test is performed. Thus, on subsequent tests, by using the same visual field grid sheet 100 previously used, the new very small diseased blind areas can be differentiated from the previous areas because the colors will be different.

Figure 5A:
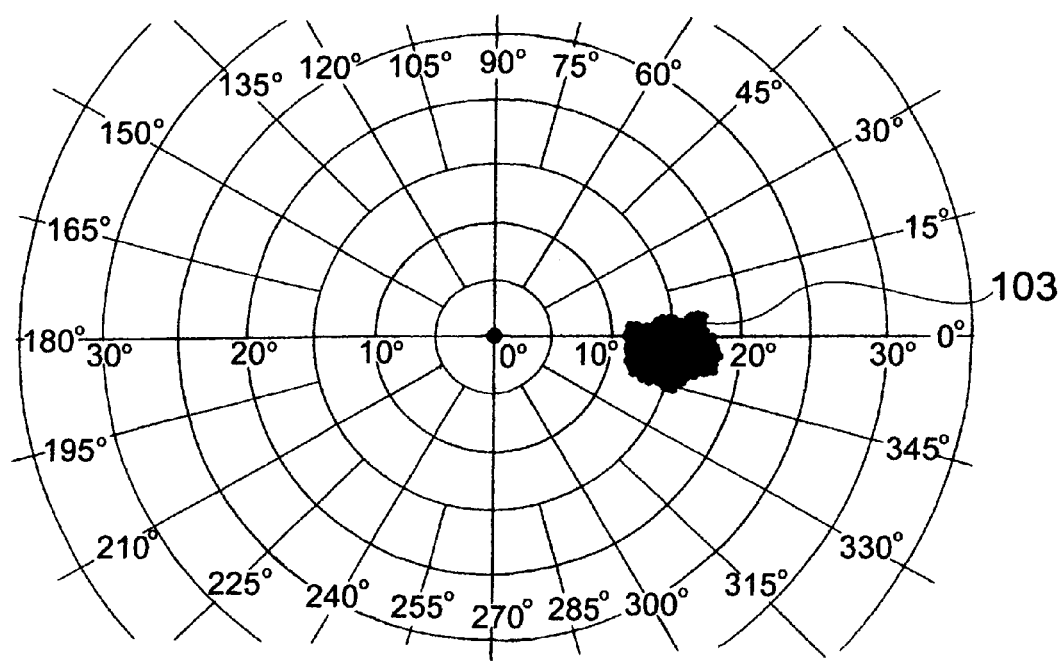
FIG. 5A is a test result of a normal eye of one of the present inventors using the present invention, which shows that a natural blind spot is a polygon.
Figure 5B:
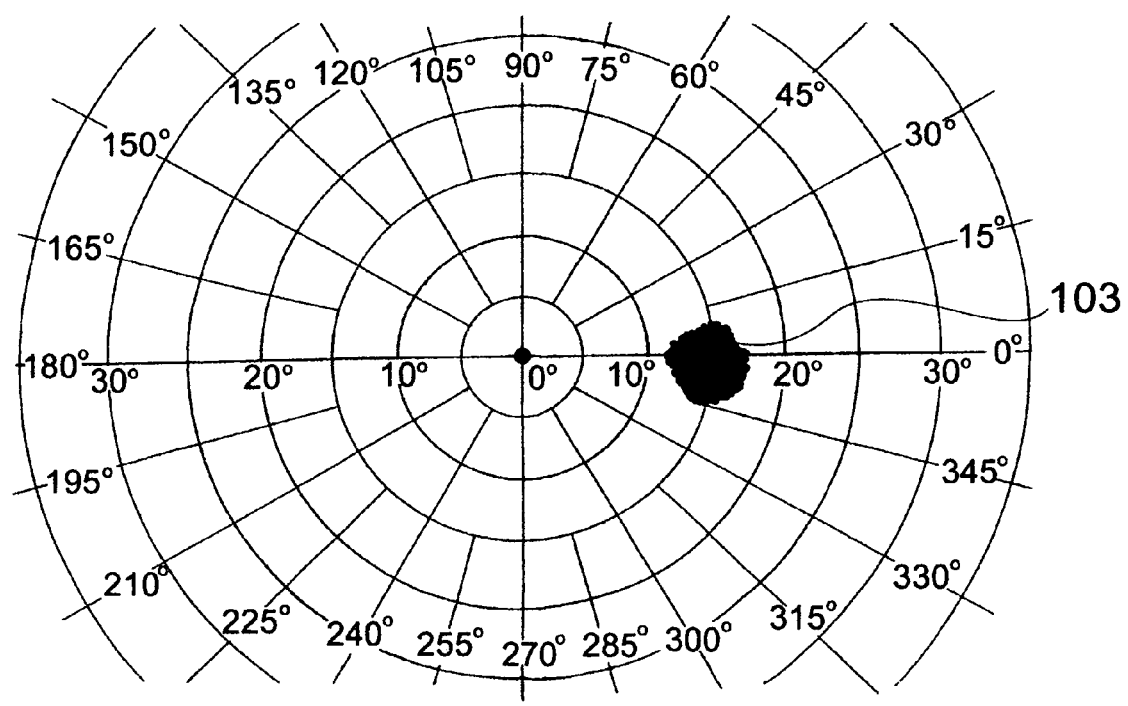
FIG. 5B is a test result of a normal eye of another present inventor using the present invention, which shows that a natural blind spot is a polygon.

Natural Blind Spot and New Discovery: FIGS. 5*a*-5*b*

It is well known that everyone has a blind spot at the location where the optic nerve from the brain enters the eye. Because this natural blind spot is not covered with retinal cells, it cannot perceive light. Eye diseases such as glaucoma, macular degeneration, and so forth will cause visual loss in other parts of the visual field. These visual loss areas caused by diseases will be called "diseased blind areas."

Before the present invention, only the approximate location of the natural blind spot in the visual field was known, and there was no visual field tester that was accurate enough to map out the shape of the natural blind spot in the visual field grid sheet. The natural blind spot is only known to exist between the 10 degree and 20 degree visual angles, on around the negative x-axis for the left eye and on around the positive x-axis for the right eye.

With the present invention, for the first time, the exact shape, size, and location of the natural blind spot has been found by the present inventors as shown in FIGS. 5A and 5B. FIGS. 5A and 5B are reduced copies from the original visual field grid sheet of 11"×17" for the right eye natural blind spot. Inside the natural blind spot, nothing can be seen; hence, test mark 97 cannot be seen when scanning inside a natural blind spot 103. When test mark 97 is moved across the boundary of natural blind spot 103 from inside to the outside, the user's perception of test mark 97 changes from being completely invisible to being clearly visible, with no transition or blurred image in between. Thus, the boundary of natural blind spot 103 can be precisely located and mapped (stamped) on visual field grid sheet 100.

Figure 6A:
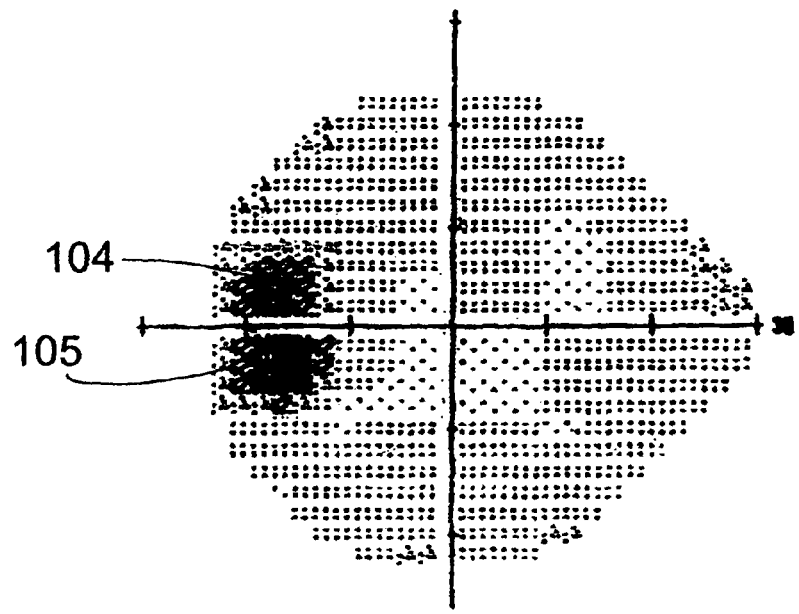
FIG. 6A is a test result of a glaucoma patient obtained from a SAP machine; the name of the patient will not be revealed to protect privacy.
Figure 6B:
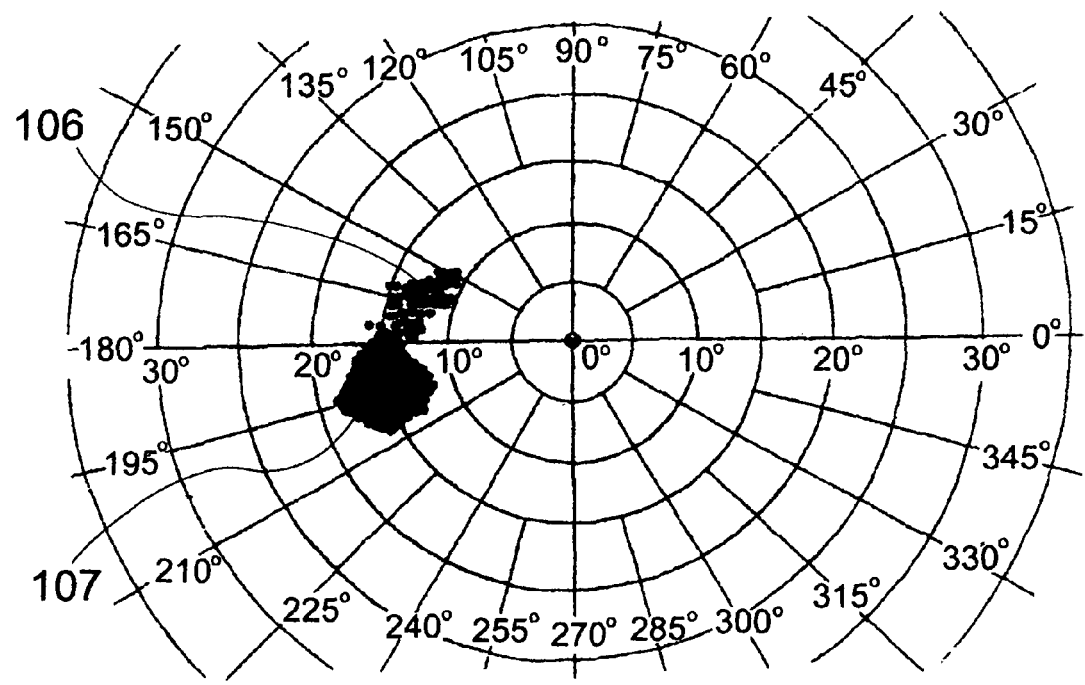
FIG. 6B is a test result using the present invention of the same patient from FIG. 6A.

FIGS. 5A and 5B show that the shape and the size of natural blind spot 103 are different from person to person. It is not a circle, rather a polygon of five sides (FIGS. 5A and 5B) or four sides (FIG. 6B). Note that in FIG. 5A, one side (the upper side) of the polygon is not straight.

The ability of the present invention to precisely map the natural blind spot will help doctors to diagnose the progression of patients' eye diseases and help researchers to correlate the blind spot shape and/or size with some diseases including eye diseases, brain tumors, and so forth, because changes to blind spot shape and/or size are important in the detection of such diseases.

Accurate Detection of Diseased Blind Areas: FIGS. 6*a*-6*b*

The prominent advantages of the present invention are the detailed and clear scanning results, which enables one to early detect vision loss related to eye diseases such as glaucoma, macular degeneration, . . . etc. In visual field tests with SAPs, that are used by eye doctors today, the light appears at only a limited number of points in the visual field. Therefore, the whole visual field is not covered by the test and some very small blind areas which occur at early stages of the disease will most likely be undetected. In the present invention, test mark 97 can scan the entire visual field so that no very small diseased blind area will escape from detection.

Furthermore, the detail and clarity in the scanning result of the present invention enables one to differentiate the diseased blind area from the natural blind spot around the natural blind spot area as in contrast to the SAP test used by doctors today, which shows the diseased blind area and the natural blind spot as one fuzzy lump, causing doctors to misdiagnose as described in the following. FIG. 6A is the test result taken with a SAP of the left eye of a glaucoma patient, whose name will not be revealed to protect privacy. Note that in this machine plot of FIG. 6A, doctors knew that two fuzzy lumps 104 and 105 were actually one single fuzzy lump, which was just separated by the negative x-axis and its scale. Two of the patient's doctors, including one glaucoma specialist, knew that fuzzy lumps 104 and 105 were at the approximate location of the natural blind spot. Therefore, both doctors told the patient that fuzzy lumps 104 and 105 were just the natural blind spot and that there was no diseased blind area there. A week prior to the doctor's tests, the patient used the present invention to scan the same eye, and the result is shown in FIG. 6B. It was a trial test with no charge to the patient. The result as shown in FIG. 6B was amazing. FIG. 6B clearly shows two distinct blind areas: (1) A normal left eye natural blind spot 107 which is about the same size but in the opposite location of the right eye's natural blind spot 103 of FIG. 5. (2) A diseased blind area 106 which has no definite shape and is clearly distinguishable from natural blind spot 107. Thus it is seen that the present invention is able to detect the diseased blind areas in the vicinity of the natural blind spot because of its detail and clarity.

We claim:

1. A high precision visual field tester comprising:
a recording surface for marking;
an eye fixation point marked on said recording surface to fixate a patient's eye visual field relative to said recording surface;
a handheld scanning device for hand movement over said recording surface by said patient, said scanning device having a visual test mark thereon for visual recognition by said patient, and an ink marker stamp on an underside of said scanning device which is aligned with said test mark for marking a spot with ink on said recording surface in registration with the position of said test mark; and
means for actuating said ink marker stamp by said patient for ink marking said recording surface.

2. The high precision visual field tester of claim 1, wherein said handheld scanning device is comprised of a horizontally oriented stick which is moved downwardly by said patient for actuating said ink marker stamp.

3. The high precision visual field tester of claim 1, including a head support for positioning the head of said patient to be tested and thereby positioning an eye of said patient in fixed spaced relationship from said recording surface.

4. The high precision visual field tester of claim 3, wherein said head support includes a rigid frame with an opening for said patient's face to rest comfortably in and a plurality of support members supporting said rigid frame whereby an eye of said patient is maintained in fixed spaced relationship from said recording surface.

5. The high precision visual field tester of claim 4, wherein said head support is provided with a chin positioner.

6. The high precision visual field tester of claim 4, further including means for aligning the center line of said patient's face relative to said recording surface whereby test results therefrom are reproduceable.

7. The high precision visual field tester of claim 1, said recording surface consisting of a grid sheet.

\* \* \* \* \*